US00PP35912P2

(12) United States Plant Patent
Whitcomb

(10) Patent No.: US PP35,912 P2
(45) Date of Patent: Jul. 2, 2024

(54) RIVER BIRCH TREE NAMED 'WHIT XXVI'

(50) Latin Name: *Betula nigra*
Varietal Denomination: Whit XXVI

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 18/445,561

(22) Filed: Oct. 19, 2023

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

(56) References Cited

U.S. PATENT DOCUMENTS

| | | | |
|---|---|---|---|
| PP10,963 | P | 6/1999 | Cheng et al. |
| PP12,768 | P2 | 7/2002 | Piney, Jr. |
| PP16,573 | P3 | 5/2006 | Whitcomb |

*Primary Examiner* — Karen M Redden
(74) *Attorney, Agent, or Firm* — Jeffrey L. Streets

(57) ABSTRACT

The new and distinct variety of river birch tree, *Betula nigra*, which was given the cultivar name 'Whit XXVI', is characterized as having a tree form that is broadly pyramidal to oval and may grow with a single or multiple stems for greater landscape appeal. The bark of the 'Whit XXVI' is distinctly orange during late summer after the greatest stem diameter increase and remains so throughout the winter with only moderate darkening, but remaining orange in color. Bark coloration begins at about one inch diameter and remains. The leaves of 'Whit XXVI' are dark green and slightly smaller in size and more plentiful than a typical river birch seedling. In one example, 'Whit XXVI' averaged about 1.15 leaves per inch of twig while the typical river birch seedling averaged about 0.7 leaves per inch of twig.

4 Drawing Sheets

Genus, species: *Betula nigra.*
Varietal denomination: 'Whit XXVI'.

BACKGROUND OF THE INVENTION

Field of the Invention

The present invention relates to a new and distinct variety or cultivar of the deciduous tree, *Betula nigra*, commonly known as river birch.

Description of the Related Art

River birch trees are native to stream banks and wet areas over much of the eastern half of the United States extending westward to central and northern Oklahoma. A river birch tree is typically about 30 to 60 feet tall, having a broad spreading crown and a short, thick soon branching trunk that is rarely larger than between 12 and 24 inches in diameter. The bark is variable among seedlings, typically reddish brown to silvery gray, shiny and becomes fissured, separating into papery scales.

The inventor of this new and distinct river birch gathered seed from the western most native river birch trees in Oklahoma in 1987, located along a narrow stream that was typically without flowing water for six months or more each year. The hypothesis was that by using seeds from these trees, additional drought tolerance might be found in subsequent seedlings. After planting, only a fraction of the seeds germinated with only one of the seedlings deemed to have ornamental value. Allowed to grow in a field near Stillwater, OK for five years, this seedling produced a few viable seeds.

One of those seedlings resulted in U.S. Plant Pat. No. 16,573 P3 and was named 'Whit XXV'.

BRIEF SUMMARY OF THE INVENTION

The new and distinct variety of river birch tree, *Betula nigra*, was given the cultivar name 'Whit XXVI'. 'Whit XXVI' is characterized as having a tree form that is broadly pyramidal to oval and may grow with a single or multiple stems for greater landscape appeal. The bark of the 'Whit XXVI' is distinctly orange during late summer after the greatest stem diameter increase and remains so throughout the winter with only moderate darkening, but remaining orange in color. Bark coloration begins at about one inch diameter and remains. The leaves are dark green and slightly smaller in size and more plentiful. For example, in September 2023, twenty (20) young branches (replications) of the current growing season of the river birch tree 'Whit XXVI' were counted, recorded and compared with a typical river birch seedling about 50 feet away and growing in the same soil and environmental conditions. The river birch tree of this invention, named 'Whit XXVI' averaged 1.15 leaves per inch while the seedling river birch averaged 0.7.

This new and distinct plant was first asexually reproduced rooting softwood cuttings from the original plant near Stillwater, OK. The asexually reproduced plants show the same unique features that characterize this new river birch tree indicating that the unique features of the plant are stable through successive generations of asexual reproduction.

BRIEF DESCRIPTIONS OF THE DRAWINGS

DETAILED BOTANICAL DESCRIPTION

The following botanical description is of the new and distinct cultivar of the river birch tree, *Betula nigra*, named 'Whit XXVI'. Specific color designations set forth by number designations are in accordance with The Royal Horticultural Society Colour Chart published in 1966. General color recitations are consistent with ordinary American color terminology.

The river birch tree 'Whit XXVI' has not been observed under all possible environmental conditions. It is to be understood that the phenotype may vary significantly with variations in environment such as soils, temperature, light intensity, and length of day, without any differences in the genotype of the plant. The following botanical characteristics and observations are taken from the plant when grown under normal outdoor conditions in north central Oklahoma. The described plant was about 17 years old growing in a field in north central Oklahoma in September 2023.

Following the growth and development of the one unique parent plant noted above, again a few seeds were produced, collected and planted in 2006. From those few seedlings, one was saved and planted in a remote corner of a field. The unique river birch tree of this invention, now 17 years old, has grown slowly and developed distinct orange bark, thick branching habit and leaf density and greater drought tolerance than other river birch seedlings grown on this farm.

The new plant of this invention is characterized as having distinctly orange bark when stems approach about one inch stem diameter. The leaves are dark green, slightly smaller than typical river birch seedlings and turn yellow in the fall. The bark of a typical river birch tree develops a reddish-brown to silvery grey color, becomes fissured and separates into papery scales with age. This new invention is also characterized as being exceptionally drought resistant. For example, during the severe heat and drought of summer 2022, other river birch trees on the farm lost an estimated 10 to 40 percent of their leaves and became less attractive. On the other hand, this unique tree named 'Whit XXVI' lost no leaves and remained attractive throughout the growing season while receiving no irrigation.

Figure 4:
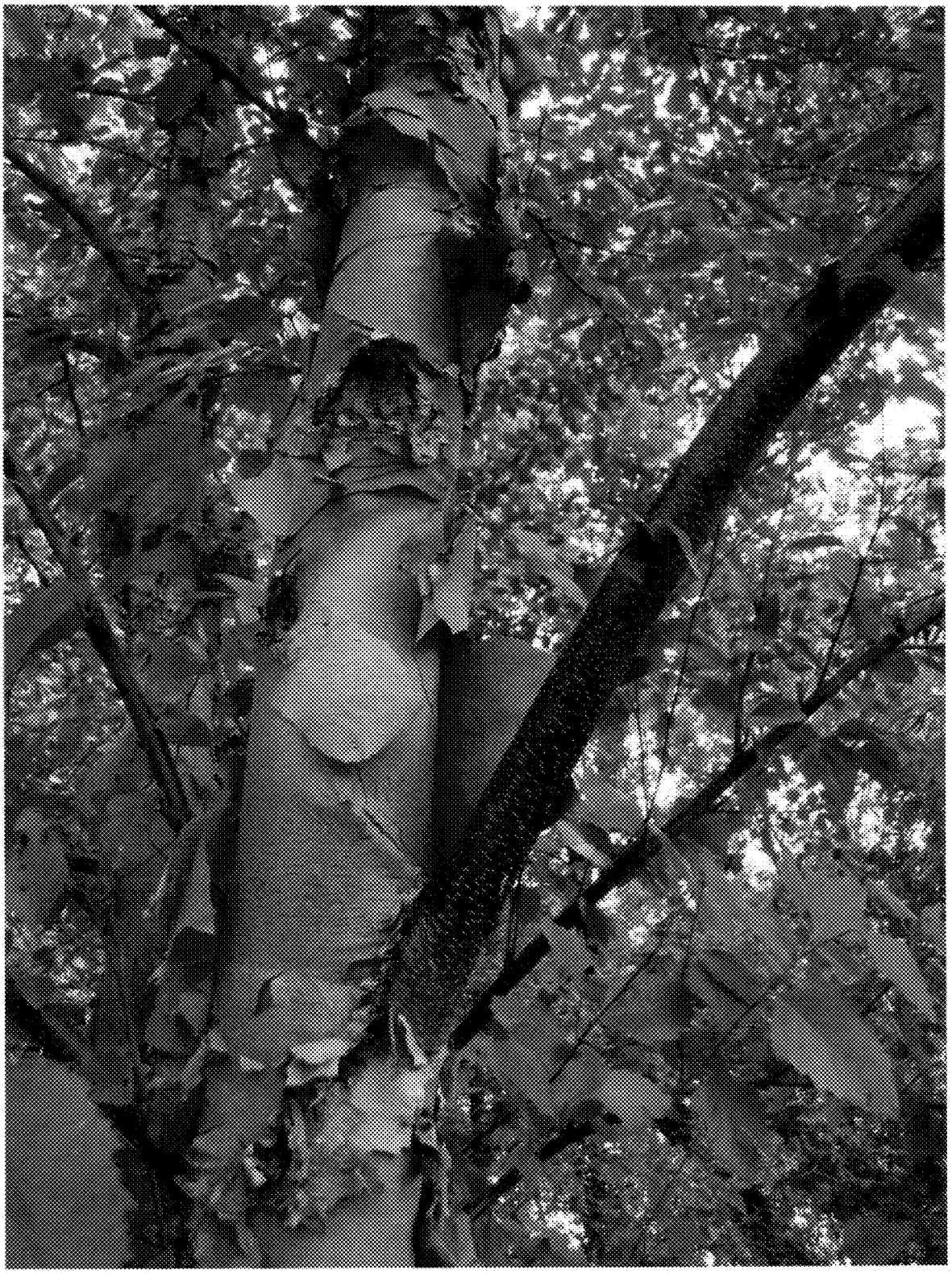
FIG. 4 is a is a full color photographic view of the young bark peeled away by expansion of the stem in early fall to expose the orange bark on limbs about 1 ich in diameter or larger.

The river birch that is known to the inventor and appears to be most similar to that of the claimed river birch named 'Whit XXVI' is the river birch described in U.S. Plant Pat. No. 16,573 P3 and named 'Whit XXV', and subsequently given the trademarked name City Slicker®. This is not surprising since the two distinct varieties ('Whit XXVI' and 'Whit XXV') share the same background and one common parent. River birch trees are wind pollinated and thus the second parent is unknown. Another river birch that is known to the inventor and appears somewhat similar to the claimed river birch tree is the DURA-HEAT® river birch tree. However, the DURA-HEAT® cultivar has variable dark tan to brown bark and coarse peeling bark sections when grown under Stillwater, OK conditions. The claimed river birch tree has dramatically different bark as shown in FIG. 4.

The plant:

*Type.*—Woody tree with single or multiple stems.

*Classification.*—River birch tree, *Betula nigra.*

*Growth habit.*—Moderately pyramidal when young, more oval with age.

*Origin.*—An open pollinated seedling from a river birch selection and breeding program near Stillwater, OK.

*Parentage.*—The inventor of this new and distance river birch gathered seed from the western most native river trees in Oklahoma in 1987 located along a narrow stream that was typically without flowing water for six months or more each year. After planting, only a fraction of the seeds germinated with only one of the seedlings deemed to have ornamental value. Allowed to grow in a field near Stillwater, Oklahoma for five years, this seedling produced few viable seeds. One of those seedlings resulted in U.S. Plant Pat. No. 16,573 P3 and named 'Whit XXV'. As previously stated, "Whit XXV" described in U.S. Plant Pat. No. 16,573 P3 and "Whit XXVI" described and claimed herein had one common parent. However, that one common parent was removed long ago following storm damage, such that no current detailed comparison can be made. Still, the parent produced flowers and viable seeds/fruits twice, once in 1992 when six years old and again in 2006 when 20 years old. Since river birch are wind pollinated, the second parent remains unknown. Following the growth and development of the one unique parent plant noted in the paragraph above, in 2006 again a few seeds were produced, collected, and planted. From those few seedlings, one was saved and planted in a remote corner of a field. In 2019, trees in the adjacent field were removed providing more light and reduced competition to this river birch seedling stimulating additional growth. In 2020 fertilizer was applied in spring and vibrant growth resulted and close evaluation began. The plant of this invention is now 17 years old. This unique river birch tree, once given improved growing conditions, developed distinct orange bark, thick branching habit and leaf density and greater drought tolerance vs other river birch seedlings grown on this farm.

*Propagation.*—The plant is easy to propagate from softwood cuttings taken in May, June or July in north central Oklahoma, with the distinguishing characteristics of the asexually propagated offspring remaining identical to the parent.

Figure 1:
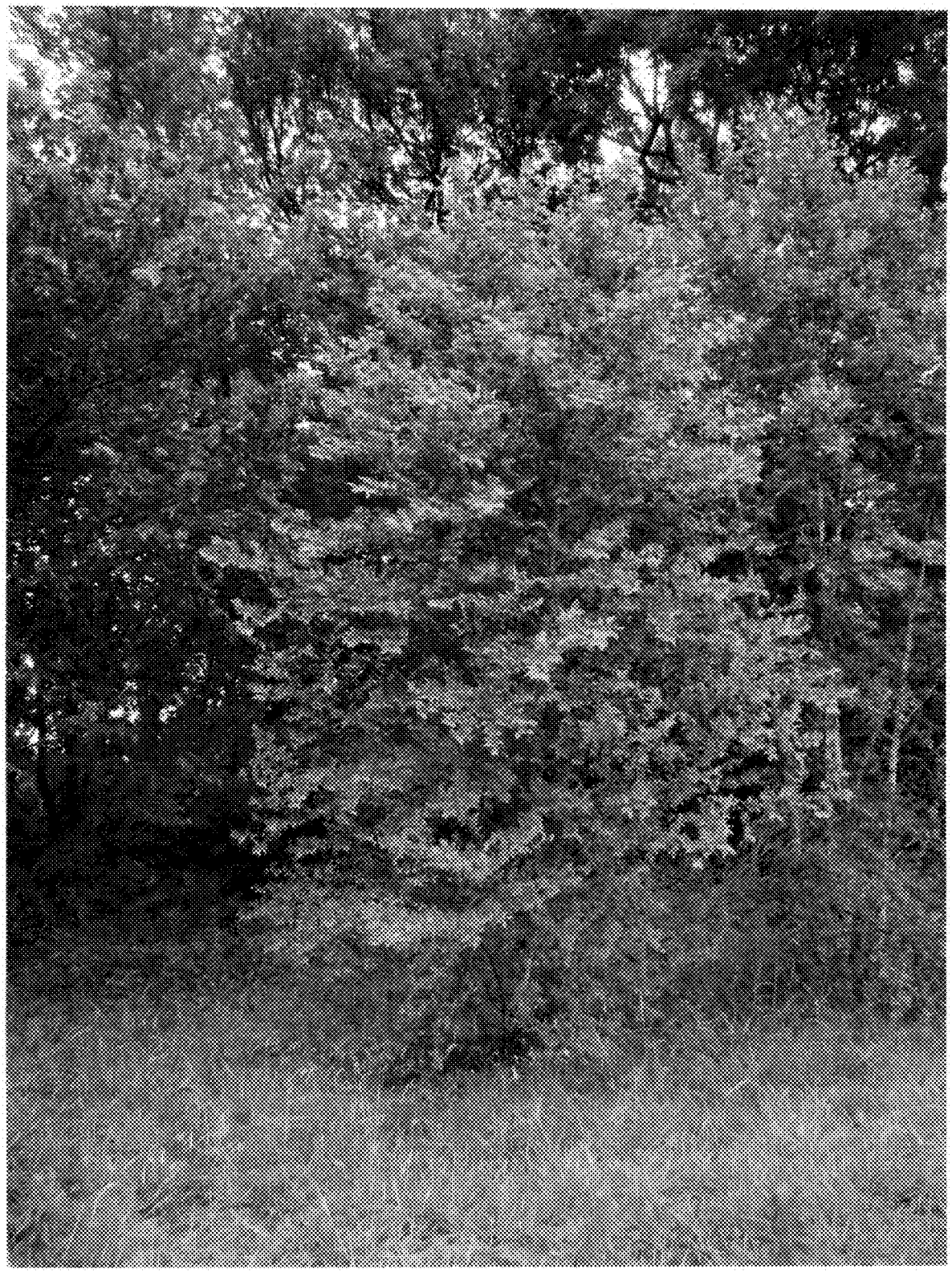
FIG. 1 is a full color photographic view of my new river birch tree.

*Size and shape.*—The growth habit of this unique river birch tree named 'Whit XXVI' is moderately pyramidal when young and is expected to be more oval with age. The tree may be grown with either a single stem or, to provide a more ornamental look, may be grown with multiple stems that are created by timely pruning. The growth rate of the asexually propagated offspring is vigorous in late spring and continues into summer. Branches are produced in abundance and are typically removed from the lower portion of the stems to expose the orange bark. In north central Oklahoma, the plant size is characterized as having a height of about 30 feet to about 50 feet. The specimen shown in the Figures is 17 years old and is shown in FIG. 1 to be approx. 16 feet tall with a spread of about 12 ft.

*Hardiness.*—USDA hardiness zones 5 through 9.

*General health and pest susceptibility.*—The foliage of 'Whit XXVI' cultivar has remained pest free. The plant is characterized as being resistant to bronze birch borer and (*Agrilus anxins*) and leaf spot disease (*Gloeosporium betularum*).

The foliage:

*Leaf persistence.*—Deciduous.

*Leaf arrangement on stems.*—Alternate.

Figure 2:
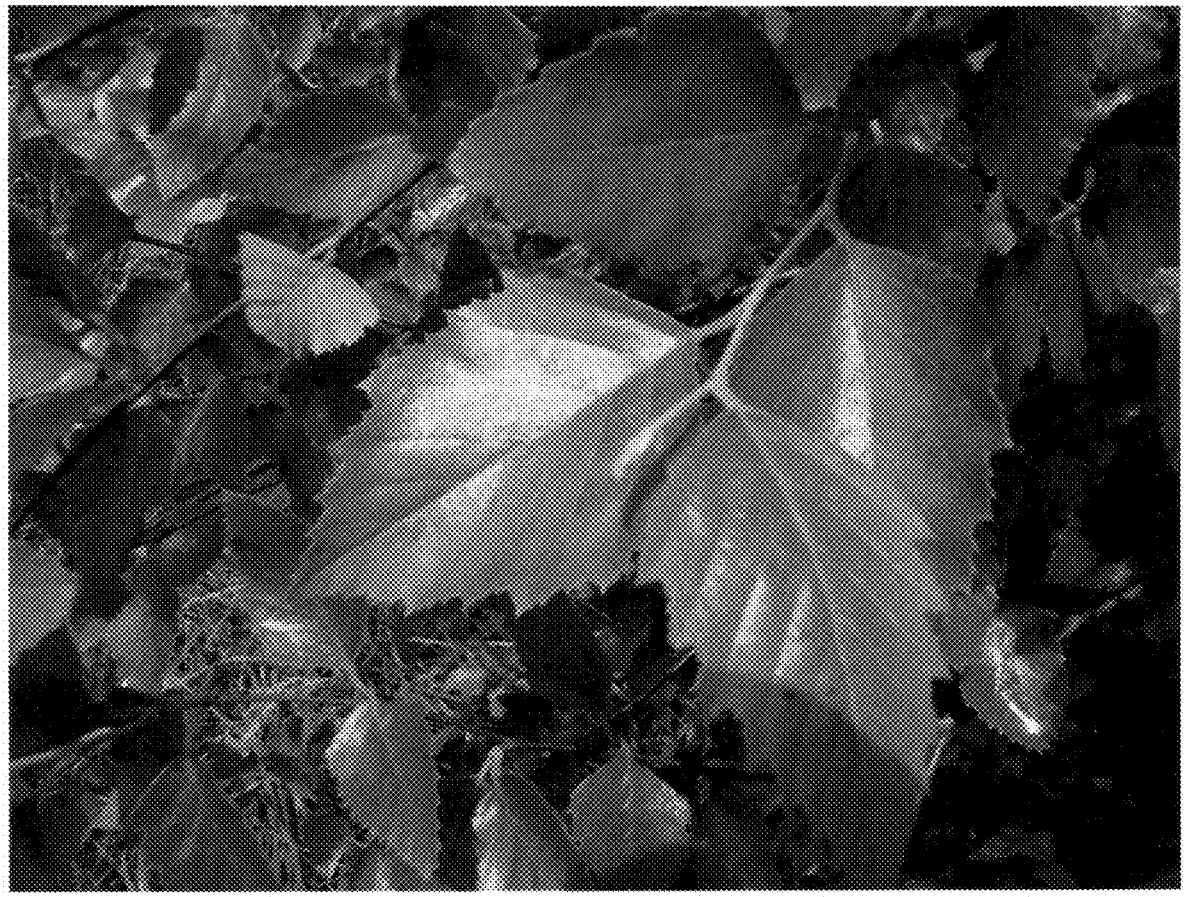
FIG. 2 is a full color photographic view of new foliage in spring on my new river birch tree showing lighter green new leaves that soon transition to dark green.
Figure 3:
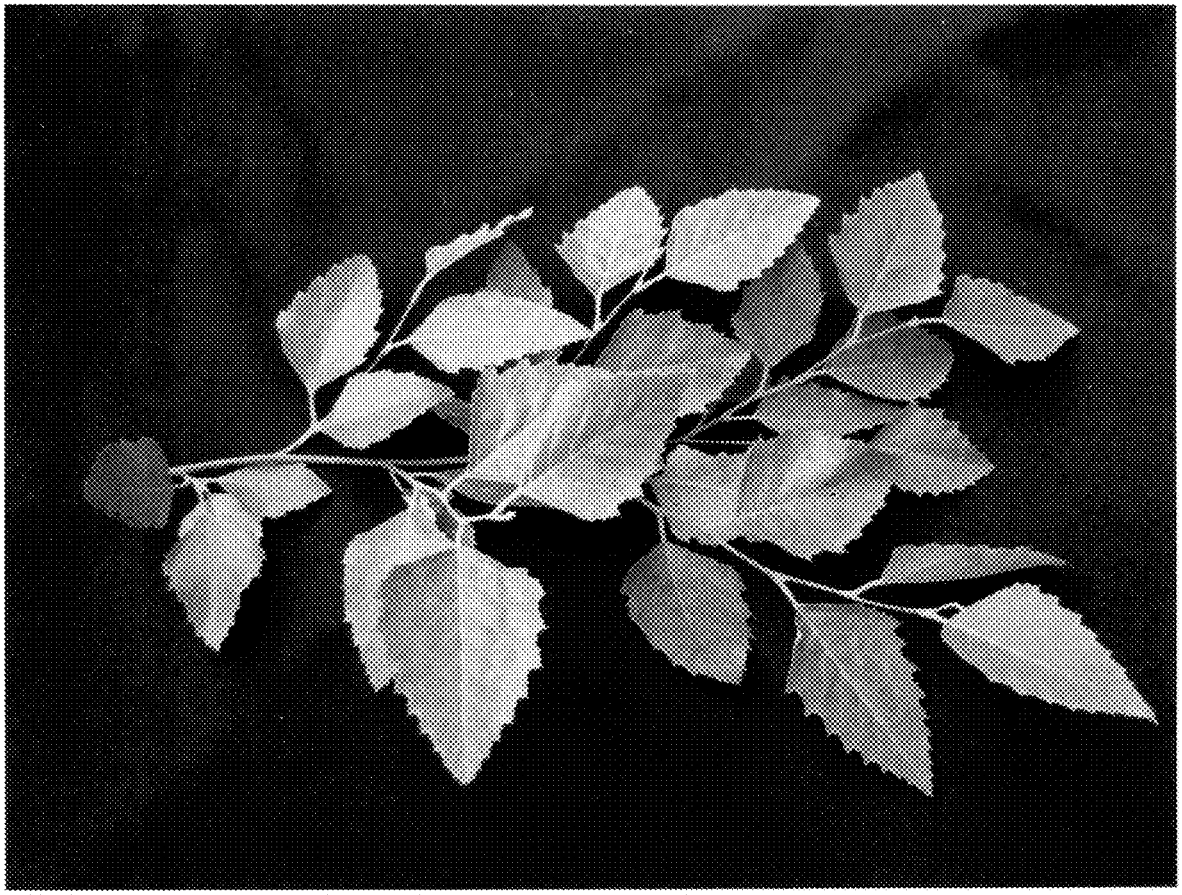
FIG. 3 is a full color photographic view of foliage of my new river birch tree in late summer, showing retention of leaves and absence of any leaf scorch or marginal burning due to heat and drought.

*Leaf shape.*—As shown in FIGS. 2 and 3 the leaves are oval, short-pointed, and slightly wedge shaped at the base. Typically, the leaves have from 5 to 7 main veins, occasionally 9 main veins on each side of the midrib.

*Leaf size.*—The leaves are between about 1.25 and 2.5 inches long and between about 1.0 to 1.75 inches wide.

*Leaf margin.*—Dentate, each dentate showing between about 2 and about 5 smaller serrations.

*Leaf quantity.*—Single leaves alternate on the twig.

*Leaf color.*—During the growing season the upper leaf surface is about 147 A or B or 148 A. The lower leaf surface is yellow green, 148 B or C on young leaves and grey-green 191 A or B on fully expanded leaves with the midveins being grayish 160 A. The fall color of the leaves is about yellow-gold 22 A or B.

*Leaf surface texture.*—The upper leaf surface has a slight rough texture and feels thick and tough. The under leaf surface has a softer texture due to pubescence distribution.

*Leaf petiole.*—The leaf petiole is between about 0.2 and about 0.5 inches long. The surface texture of the leaf petiole is similar to that of the underside of the leaf in that it is pubescent, which gives it the grayish (160 A) color.

*Stipules.*—None.

*Stems.*—The numerous stems are characterized as being slender, spreading, and flexible.

*Stem color and texture.*—Young stems of current season have prominent lenticels and surfaces are about 177 A or B up to about one inch when bark shedding begins. The number and color of lenticels is extremely variable and not different than known cultivars of river birch trees. The color designation of the lenticels most often in the 156 A or B or C range but quite variable. Dormant buds are variable in color and size. On the sides of the buds that are exposed to sun the color is about 165-A or B, while on the shaded side are about 164-A or B. Bud size is variable but about 3/32 inch long by about 1/32 inch wide. The early peeling bark pieces on young stems between about 0.75 and one inch are dark tan, 166 A or B. By mid-September in central Oklahoma, the exposed bark on stems having a diameter of about one inch or larger is distinctly orange 170 A or B or 26 A or B in orange group.

Flowers: No flowers have been produced to date.

Fruits: No fruits have been produced to date.

I claim:

1. A new and distinct variety of river birch tree named 'WHIT XXVI', substantially as illustrated and described herein.

* * * * *